United States Patent
Grant et al.

(10) Patent No.: US 6,524,794 B1
(45) Date of Patent: Feb. 25, 2003

(54) IDENTICAL-BY-DESCENT FRAGMENT ENRICHMENT

(75) Inventors: Struan Grant, Reykjavik (IS); Thorarinn Blöndal, Gardabaer (IS)

(73) Assignee: deCode genetics ehf., Reykjavik (IS)

( * ) Notice: Subject to any disclaimer, the term of this patent is extended or adjusted under 35 U.S.C. 154(b) by 0 days.

(21) Appl. No.: 09/429,999

(22) Filed: Oct. 29, 1999

(51) Int. Cl.[7] ................................................. C12Q 1/68
(52) U.S. Cl. ........................ 435/6; 435/91.1; 435/91.2; 536/25.3
(58) Field of Search .......................... 435/6, 91.1, 91.2; 536/25.3

(56) References Cited

U.S. PATENT DOCUMENTS

| | | | |
|---|---|---|---|
| 5,132,207 A | 7/1992 | Kohne et al. ................. | 435/6 |
| 5,376,526 A | 12/1994 | Brown et al. ................. | 435/6 |
| 5,571,676 A | 11/1996 | Shuber ......................... | 435/6 |
| 5,679,522 A | 10/1997 | Modrich et al. .............. | 435/6 |
| 5,698,400 A | 12/1997 | Cotton et al. ................. | 435/6 |
| 5,702,894 A | 12/1997 | Modrich et al. .............. | 435/6 |
| 5,721,098 A | * 2/1998 | Pinkel et al. ................. | 435/6 |
| 5,824,471 A | 10/1998 | Mashal et al. ................ | 435/6 |
| 5,851,770 A | 12/1998 | Babon et al. .................. | 435/6 |
| 5,858,754 A | 1/1999 | Modrich et al. ............. | 435/195 |
| 5,876,929 A | * 3/1999 | Wigler et al. ................ | 435/6 |
| 5,876,941 A | 3/1999 | Landegren et al. ........... | 435/6 |
| 5,958,692 A | 9/1999 | Cotton et al. ................. | 435/6 |
| 6,027,898 A | * 2/2000 | Gjerde et al. ................. | 435/6 |

FOREIGN PATENT DOCUMENTS

| | | |
|---|---|---|
| WO | WO 93/18186 | 9/1993 |
| WO | WO 95/12688 | 5/1995 |
| WO | WO 96/35809 | 11/1996 |
| WO | WO 96/41002 | 12/1996 |
| WO | WO 99/35486 | 7/1999 |
| WO | WO 99/35602 | 7/1999 |
| WO | WO 00/46402 | 8/2000 |

OTHER PUBLICATIONS

Straus et al. PNAS USA. 1990. vol. 87 p. 1889–1893.*
Dean, M., "Resolving DNA mutations", *Nature Genetics*, 9:103–104 (1995).
Marshal, R.D., et al., "Detection of mutations by cleavage of DNA heteroduplexes with bacteriophage resolvases", *Nature Genetics*, 9:177–183 (1995).
Mashal, R.D., et al., "Enzyme Mismatch Cleavage—Bacteriophage Resolvases", *Laboratory Methods for the Detection of Mutations and Polymorphisms IN*, pp. 217–223 (1997).
Chung I, et al., "The use of cloned repetitive sequences as hybridization competitors to detect single copy sequences", *Genetic Analysis:Biomelecular Engineering*, 14(1) :13–15 (1997).
Asgeirsson, B., et al., "Hereditary Cystatin C Amyloid Angiopathy: Monitoring the Presence of the Leu–68→ Gln Cystatin C Variant in Cerebrospinal Fluids and Monocyte Cultures by MS," *Biochem. J.*, 329 (3) :497–503 (1998).
Cheung, V.G. and Nelson, S.F., "Genomic Mismatch Scanning Identifies Human Genomic DNA Shared Identical by Descent," *Genomics*, 47:1–6 (1998).
Cheung, V.G., et al., "Linkage–disequilibrium Mapping Without Genotyping," *Nature Genetics*, 18:225–230 (1998).
Jonsdottir, S. and Palsdottir, A., "Molecular Diagnosis of Hereditary Cystatin C Amyloid Angiopathy," *Biochem. Medicine and Metabolic Biol.*, 49:117–123 (1993).
Kruglyak, L. and McAllister, L., "Who Needs Genetic Markers?," *Nature Genetics*, 18:200–202 (1998).
Levy, E., et al., "Stroke in Icelandic Patients with Hereditary Amyloid Angiopathy is Related to a Mutation in the Cystatin C Gene in Inhibitor of Cysteine Proteases," *J. Exp. Med.*, 169:1771–1778 (1989).
McAllister, L., et al., "Enrichment for Loci Identical–by–Descent between Pairs of Mouse or Human Genomes by Genomic Mismatch Scanning," *Genomics*, 47:7–11 (1998).
Mirzayans, F., et al., "Identification of the Human Chromosomal Region Containing the Iridogoniodysgenesis Anomaly Locus by Genomic–Mismatch Scanning," *Am. J. Hum. Genet.*, 61:111–119 (1997).
Nelson, S.F., "Genomic Mismatch Scanning: Current Progress and Potential Applications," *Electrophoresis*, 16:279–285 (1995).
Wei, L., et al., "Instability of the Amyloidogenic Cystatin C Variant of Hereditary Cerebral Hemorrhage with Amyloidosis, Icelandic Type," *J. Bio. Chem.*, 273(19):11806–11814 (1998).

* cited by examiner

*Primary Examiner*—W. Gary Jones
*Assistant Examiner*—Juliet C. Einsmann
(74) *Attorney, Agent, or Firm*—Hamilton, Brook, Smith & Reynolds, P.C.

(57) ABSTRACT

Methods of identifying DNA fragments comprising DNA that is identical by descent for two individuals are disclosed. The methods comprise obtaining a sample of genomic DNA from each of two individuals; contacting the samples of genomic DNA with a restriction endonuclease; methylating one of the DNA samples; mixing the methylated DNA sample and the unmethylated DNA sample, and incubating the DNA sample mixture under denaturing conditions; further incubating the DNA sample mixture under conditions which allow re-annealing of the DNA samples to form a mixture comprising homohybrid DNA fragments and heterohybrid DNA fragments; contacting the mixture with restriction endonuclease(s) which digest homohybrid DNA fragments; contacting the mixture with an endonuclease(s) which cleaves both strands of a mismatch-containing heterohybrid DNA fragment, to form a DNA sample mixture comprising perfectly-matched heterohybrid DNA fragments which are enriched in DNA fragments that are identical by descent for the two individuals.

28 Claims, 1 Drawing Sheet

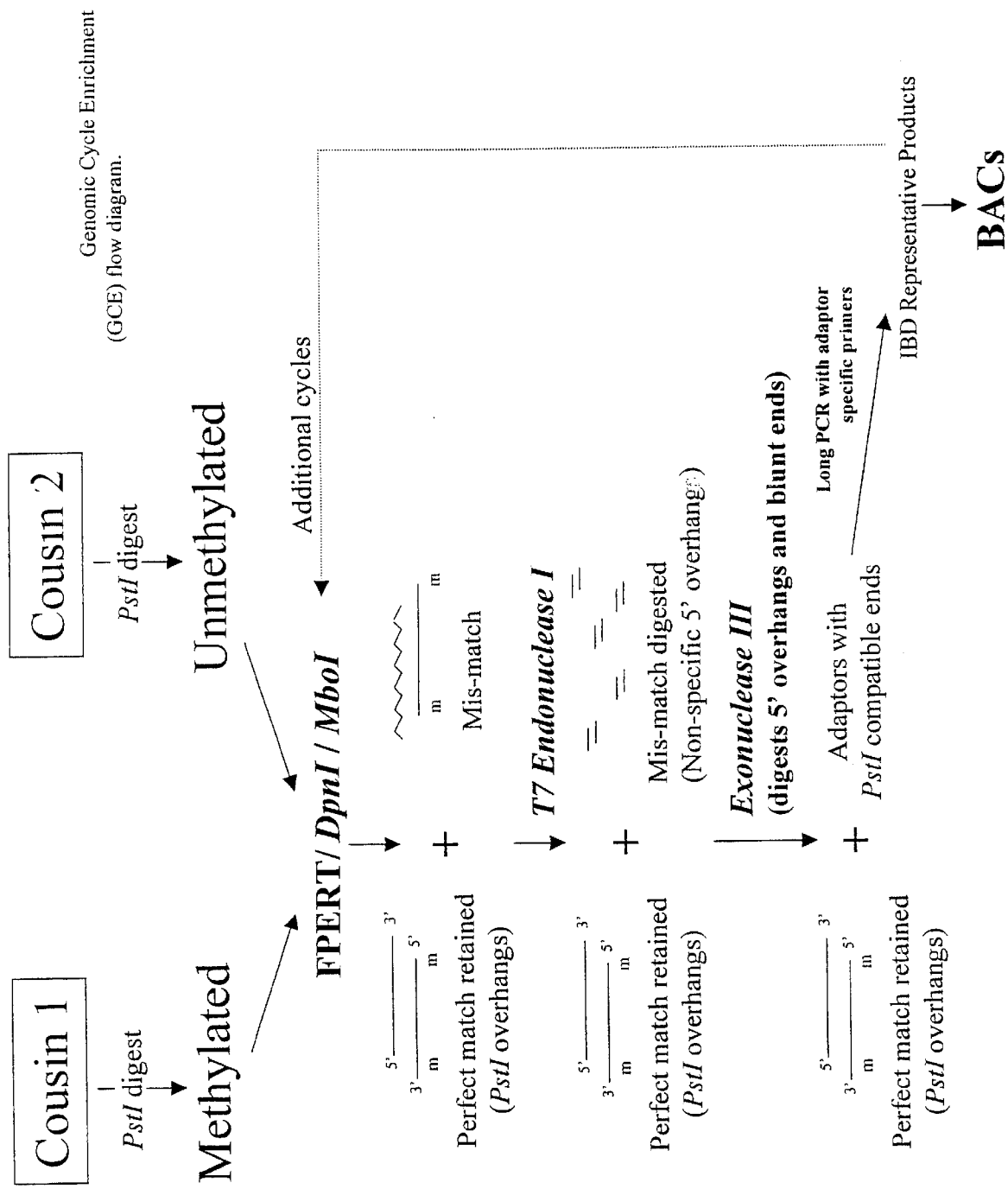

IDENTICAL-BY-DESCENT FRAGMENT ENRICHMENT

BACKGROUND OF THE INVENTION

As understanding of the role of genetic alterations in the basis of disease has increased, methods have been developed to facilitate identification of disease-causing mutations. Recently, a method of genomic mismatch scanning (GMS) has been used to identif regions of DNA that are "identical by descent" ("IBD") in individuals who are distantly related, that is, regions of DNA that are inherited from a common ancestor (see, e.g., U.S. Pat. No. 5,376,526 to Brown et al; Nelson, S. F., *Electrophoresis* 16:279–285 (1995); Cheung, V. G. et al., *Nature Genetics* 18:225–230 (1998); and Cheung, V. G. and Nelson, S. F., *Genomics* 47:1–6 (1998)). DNA that is IBD between individuals who are distantly related, and who are affected by a disease, may contain a genetic mutation within a shared BD region that contributes to or causes the disease (see, e.g., Mirzayans, F. et al., *Am. J. Hum. Genet.* 61:111–119 (1997)). GMS methods employ a series of steps, including use of a panel of methyl-directed mismatch repair enzymes (mutH, mutL and mutS from *Escherichia coli*), and binding of mismatched fragments to benzoylated, naphthylated DEAE cellulose (BNDC). Difficulties associated with GMS methods include optimization of the mutHLS enzymes, unreliability of BNDC binding, and high background interference (see Kruglyak, L. and McAllister, L., *Nature Genetics* 18:200–202 (1998)). Easier and more accurate methods of identifying IBD regions of DNA would enhance the ability to identify mutations associated with disease.

SUMMARY OF THE INVENTION

The present invention is drawn to methods of identifying DNA fragments containing DNA that are identical by descent for two individuals. In the methods, a sample of genomic DNA is obtained from each of the two individuals. The samples are initially digested with a restriction endonuclease, such as PstI; one of the samples is then methylated, while the other is preserved as a non-methylated sample. The digested, methylated and non-methylated samples are then mixed and incubated under conditions which allow denaturation of the DNA (e.g., heating of the mixture). The denatured mixture is then allow to re-anneal, preferably in the presence of a phenol based emulsion (e.g., formamide phenol emulsion reassociation technique), forming a mixture containing homohybrid DNA fragments (both methylated homohybrids and non-methylated hybrids), and heterohybrid DNA fragments ("hemi-methylated"). The re-annealed sample is then contacted with restriction endonucleases which digest the homohybrid DNA fragments (e.g., DpnI, which digests methylated, double-stranded DNA, and MboI, which digests unmethylated, double-stranded DNA). The sample is then contacted with an endonuclease(s) which cleaves both strands of a mismatch-containing heterohybrid DNA fragment (e.g., T7 endonuclease I, which yields 5' overhangs which are exonuclease III sensitive, and can thus be digested by ExoIII). As a result of this process, the sample mixture contains and is enriched in perfectly-matched heterohybrid DNA fragments which comprise DNA fragments that are identical by descent for the two individuals. If desired, the mixture can be further processed by contact with an exonuclease which digests small fragments generated by the endonuclease(s) which cleaves both strands of a mismatch-containing heterohybrid DNA fragment. As the fragments may contain many repetitive sequences, the mixture can be incubated with repeat-rich DNA (e.g., COT-1) to hybridize and remove the repetitive sequences. In addition, the perfectly-matched heterohybrid DNA fragments can be ligated to nucleic acid adaptors and amplified by polymerase chain reaction (PCR) or long-range polymerase chain reaction (LR-PCR). To reduce background interference further, the process described above can be repeated, one or more times, using perfectly-matched heterohybrid DNA fragments as a first sample of genomic DNA, and a sample of genomic DNA from a third (or fourth, etc.,) individual as a second sample of genomic DNA. The methods of the invention provide a simple and efficient means of identifying regions of genomic DNA that are identical by descent, utilizing enzymes which significantly eliminate background interference without requiring extensive optimization of conditions.

BRIEF DESCRIPTION OF THE DRAWING

The FIGURE is a depiction of the protocol for genomic cycle enrichment (GCE), including the optional steps of ligating adaptors to identical-by-descent DNA fragments, followed by performing long-range polymerase chain reaction (PCR) with adaptor-specific primers.

DETAILED DESCRIPTION OF THE INVENTION

The invention pertains to methods for identifying DNA fragments that are identical by descent (IBD) for two individuals. As described herein, Applicants have devised simple methods which utilize denaturation and re-annealing of two samples of DNA, followed by selective digestion of particular DNA fragments, in order to yield a sample of DNA fragments that is enriched in perfectly-matched heterohybrid DNA that is IBD. The methods can be used to facilitate identification of genetic mutations that contribute to a disease which affects the two individuals.

In the methods of the invention, a test sample containing genomic DNA is obtained from each of two individuals, such as from individuals having, suspected of having, or carrying or suspected of carrying, a genetic defect which contributes to development of a disease of interest (e.g., cystic fibrosis, hereditary cerebral hemorrhage with amyloidosis (Icelandic type), or osteogenesis imperfecta)) (the "test individuals"). The genetic defect which contributes to the development of the disease need not be known; in a preferred embodiment, the genetic defect is unknown, and the methods of the invention are used to identify regions of DNA that are IBD and that therefore may contain the genetic defect. The test individual can be an adult, child or fetus. The test sample which contains genomic DNA can be from any source which contains genomic DNA, such as a blood sample, sample of amniotic fluid, sample of cerebrospinal fluid, or tissue sample from skin, muscle, placenta, gastrointestinal tract or other organs. A test sample from fetal cells or tissue can be obtained by appropriate methods, such as by amniocentesis or chorionic villus sampling. In a preferred embodiment, the test individuals are distantly related; that is, they are related by the second degree or greater (i.e., cousins, grandparent and grandchild, or more distantly related individuals). More distant relations provide greater amounts of genetic divergence, therefore increasing the likelihood that DNA fragments that are identical by descent will be fragments of interest (e.g., containing the genetic defect which contributes to the development of the disease). The test samples containing genomic DNA can be processed initially to isolate or partially purify the genomic DNA away from other cellular components, using conventional means (e.g., lysing cells, removing cellular debris, separating the DNA from proteins, lipids or other components present in the mixture) (see, for example, Molecular Cloning, A Laboratory Manual, 2nd ed. (eds. Sambrook et al.) CSHL Laboratory Press, Cold Spring Harbor, N.Y. 1989).

The test samples containing genomic DNA (referred to herein as the "first genomic DNA sample" and the "second genomic DNA sample") are initially digested with a restriction endonuclease to generate smaller fragments of DNA (referred to herein as "preliminary digest" DNA samples). In a preferred embodiment, the restriction endonuclease generates preliminary digest DNA fragments that are approximately 5 to 10 kb in length, and preferably have 3' overhangs (e.g., PstI, which generates fragments with 4 base pair 3' overhangs). Overhangs at the 3' ends are preferred specifically when exonuclease III digestion is used to eliminate mismatched heterohybrid DNAs, as described in detail below. Restriction enzymes yielding other overhangs or ends can also be used if other specific exonucleases are employed.

One of the preliminary digest DNA samples is then methylated, using standard techniques (e.g., Marinus, M. G., *Ann. Rev. Genet.* 21:113–131 (1987)). In a preferred embodiment, a sequence specific methylase, such as Dam methylase or a restriction methylase, is used so as to methylate substantially completely the sequences of the DNA from one of the sources. The other preliminary digest DNA sample is left unmethylated.

The methylated sample (the "methylated preliminary digest DNA sample") and the unmethylated sample ("unmethylated preliminary digest DNA sample) are then mixed, forming a "DNA sample mixture". The DNA sample mixture is subjected to appropriate conditions to allow the DNA in the sample to denature (forming a "denatured DNA sample mixture") and subsequently to re-anneal to form an "annealed DNA sample mixture". For example, denaturing can be performed using standard methods, such as by heating the sample mixture to approximately 85 to 99 degrees C., preferably approximately 95 degrees C. If the DNA sample mixture is denatured by heat, re-annealing occurs as the sample mixture cools. In a preferred embodiment, the efficiency of the re-annealing process is enhanced by performing the re-annealing process in the presence of a phenol-based emulsion (Formamide Phenol Emulsion Reassociation Technique (FPERT)) as described by Casna et al. (*Nucleic Acids Res.* 14:7285–7303 (1986); and Kohne, D. E. et al., *Biochemistry* 16(24):5329–41 (1977); the entire teachings of these references are incorporated by reference herein). For FPERT, the sample mixture is contacted with a FPERT mix, which contains sodium thiocyanate, Tris HCl, EDTA and formamide, resulting in an FPERT reaction mixture. The FPERT reaction mixture is then incubated in order to allow re-annealing of DNA fragments in the reaction mixture.

The FPERT reaction mixture yields an annealed DNA sample mixture containing three possible types of DNA complexes: completely methylated homohybrids, generated by re-annealing of complementary strands of DNA that originated from the sample of genomic DNA from a first individual; completely unmethylated homohybrids, generated by re-annealing of complementary strands of DNA that originated from the sample of genomic DNA from a second individual; and "hemi-methylated" heterohybrids, containing one methylated strand and one non-methylated strand of DNA, that are generated by annealing of single-stranded DNA from each individual. The hemi-methylated heterohybrids which are formed from the exact matching of single-stranded DNA from each sample represent the IBD fragments shared between the two individuals.

The annealed DNA sample mixture is then contacted with one or more restriction endonucleases, preferably methylation-sensitive restriction endonucleases, in order to selectively digest homohybrids. For example, restriction endonucleases are selected which digest either unmethylated homohybrids or methylated homohybrids, while being incapable of cleaving the hemi-methylated heterohybrids. In a preferred embodiment, the restriction endonucleases DpnI (digesting methylated homohybrids) and MboI (digesting unmethylated homohybrids) are used. Alternatively, more than one type of endonuclease can be used to target each type of homohybrid. The resultant homohybrid-digested, annealed DNA sample mixture is enriched in heterohybrid fragments. The term "enriched," as used herein, indicates that the proportion of heterohybrid fragments to other (homohybrid) fragments of the same approximate size, is relatively increased in the homohybrid-digested, annealed DNA sample mixture, when compared with an annealed DNA sample mixture that has not been exposed to selective digestion of homohybrids.

The homohybrid-digested, annealed DNA sample mixture is contacted with endonuclease(s) which selectively digest DNA heterohybrids that contain one or more mismatched base pairs, while preserving complementary perfectly-matched DNA heterohybrids. The endonuclease which selectively digests DNA heterohybrids is an endonuclease that cleaves both strands of double-stranded DNA at a point where a mismatch occurs. In a preferred embodiment, the endonuclease is an endonuclease that recognizes all 8 possible mis-matches, and is methylation-independent (e.g., T7 endonuclease I). In a preferred embodiment, the endonuclease is T7 endonuclease I. The use of T7 endonuclease I results in the production of small DNA fragments (less than approximately 5 kb) with non-specific 5' overhangs. These small fragments can be further digested using an exonuclease, such as Exonuclease III. Intact fragments (not cleaved by T7 endonuclease I) will be resistant to cleavage by exonuclease III, as they have resistant PstI 3' overhangs.

The resultant mismatch-digested sample mixture is enriched in perfectly-matched heterohybrid fragments; that is, the proportion of perfectly matched heterohybrid fragments to other (mismatch-containing) fragments of the same approximate size, is relatively increased in the mismatch-digested DNA sample mixture, when compared with an sample mixture that has not been exposed to selective digestion of mismatched heterohybrids. The mismatch-digested sample contains perfectly-matched DNA heterohybrids which comprise DNA fragments that are inherited by descent (i.e., IBD fragments).

The IBD fragments in the mismatch-digested sample mixture can then be further processed, if desired. For example, small fragments produced by digestion of mismatch containing heterohybrids can be rich in repetitive sequences. If desired, the impact of these small fragments on an analysis of the IBD fragments can be minimized, by incubating the mismatch-digested DNA sample mixture with a sample of repetitive DNA (e.g., COT-1 repetitive DNA). For example, the mismatch-digested DNA sample mixture is contacted with a sample of repeat-rich DNA, in excess, under conditions which allow the small fragments that are rich in repetitive sequences to hybridize with the repetitive DNA (e.g., the mixture is heated to denature the DNA fragments, and then allowed to cool gradually, thereby allowing small fragments that are rich in repetitive sequences to re-anneal to the repetitive DNA).

To facilitate analysis of the IBD fragments, the IBD fragments can be ligated to nucleic acid adaptors with ends that are compatible with the overhanging ends generated during the initial digestion with a restriction endonuclease (e.g., if PstI was used, the adaptors are compatible with 4 base pair 3' overhangs), using standard methods. The nucleic acid adaptors are small fragments of DNA, of approximately 15 to 40 base pairs in length, which have known sequences. In one embodiment, it is preferred that the GC content of the adaptors is equal to, or less than, approximately 60%. The adaptors facilitate manipulation of the IBD fragments, particularly if hybridization to repeat-rich DNA as described above is performed: the adaptors do not ligate to fragments which have no overhangs (i.e., do not ligate to repetitive DNA sequences because they have annealed to the repeat-rich DNA). Furthermore, if amplification of the IBD fragments is desired, polymerase chain reaction (PCR) or long-range polymerase chain reaction (LR-PCR) can be performed using adaptor-specific primers, so that only fragments with adaptors at both ends will be amplified. See generally *PCR Technology: Principles and Applications for DNA Amplification* (ed. H. A. Erlich, Freeman Press, NY, NY, 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202. In a preferred embodiment, long-range PCR is used (see, e.g., U.S. Pat. No. 5,512,462, Burland, V., and Kusukawa, N., *Biotechniques* 23:1070–1072, 1074–1075 (1997); Cheng, S. et al., *Proc. Natl. Acad. Sci. USA* 91:5695–5699 (1994)). Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA).

Certain of the IBD fragments will be shared by chance between the two test individuals, and therefore will not comprise a genomic region that contains a genetic mutation contributing to the disease of interest (the "genomic region of interest"). In order to minimize the presence of such "chance" IBD fragments and to enhance the presence of IBD fragments that may comprise the genomic region of interest (i.e., the "IBD fragments of interest"), the method described above can be repeated, utilizing the IBD fragments in place of the "first genomic DNA sample." The IBD fragments are used, together with a new genomic DNA sample from a third, distantly related individual (a "third genomic DNA sample"). The third individual, like the first and second individuals described above, is an individual who has, is suspected of having, carrying or suspected of carrying, a genetic defect which contributes to development of the disease of interest. The IBD fragments and the third genomic DNA sample are digested, and subjected to FPERT and further endonuclease and exonuclease digestion as described above. This process can be repeated in a cyclic manner, using the IBD fragments of interest generated in each cycle as a first sample of genomic DNA, and a sample of genomic DNA from a fourth, fifth, etc., individual as a second sample of genomic DNA. The cycles can be repeated as many times as desired, using the IBD fragments and genomic DNA samples from additional test individuals. The cycling process removes the IBD regions shared by chance, and enriches the amount of IBD fragments of interest.

The IBD fragments obtained by the methods described above can be analyzed for their biological function, can be used for genotyping or for genomic mapping, or can also be used as oligonucleotide probes to identify genes of interest, as well as to identify mutations in genes of interest that may contribute to a disease of interest. For example, the IBD fragments can be labeled (e.g., with $^{32}P$ through random priming, as in Smith, D. R., *Methods. Mol. Biol.* 58:27–29 (1996)), and used to probe a library, such as a bacterial artificial chromosome (BAC) library, or a gene-chip array (Hacia, J. G. and Collins, F. S., *J. Med. Genet.* 36(10):730–6 (1999)), to identify genes of interest.

The methods described herein provide a simple and expedient means for identifying regions of genomic DNA that are identical by descent. The methods describe herein utilize an enodnuclease (e.g., T7 endonuclease I) that recognizes all 8 possible-mismatches in heterohybrids, in contrast to the 7 recognized by the MutHLS system employed in genomic mismatch scanning (GMS); furthermore, the use of a single endonuclease requires significantly less optimization than the three-enzyme MutHLS system. Because the endonuclease cleaves both strands of the mismatched DNA, the cleaved fragments are subsequently digested by an exonuclease, significantly eliminating background interference. Thus, there is no need to perform additional steps (such as the benzoylated, naphthylated DEAE cellulose step in GMS) to remove single-stranded DNA fragments. In addition, background can additionally be eliminated significantly by cycling of the methods, thereby eliminating need for amplification of the IBD fragments.

The invention is further illustrated by the following Exemplification, which is not intended to be limiting. The teachings of all references cited herein are incorporated by reference in their entirety.

EXEMPLIFICATION

Identification of a Mutation Associated with Hereditary Cerebral Hemorrhage with Amyloidosis, Icelandic Type Hereditary cerebral hemorrhage with amyloidosis (Icelandic type) is a well-characterized disease, caused by a T→A point mutation in codon 68 for leucine which results in a single base change Leu68→Gln (see, e.g., Levy, E. et al., *J Exp Med* 69(5):1771–8 (1989); Johnsdottir, S. and Palsdottir, A., *Biochem Med Metab Biol* 49(2):117–23 (1993); Abrahamson, M., and Grubb, A., *Proc Natl Acad Sci USA* 91(4):1416–20 (1994); Olafsson I, et al., *Brain Pathol* 6(2):121–6 (1996); Abrahamson, M., *Scand J Clin Lab Invest Suppl* 226:47–56 (1996); Wei, L. et al., *J Biol Chem* 273(19):11806–14 (1998); Asgeirsson, B. et al., *Biochem J* 329 ( Pt 3):497–503 (1998); Benedikz, E. et al., *Amyloid* 6(3):172–82 (1999)). The mutation is routinely determined by a simple restriction fragment length polymorphism (RFLP) assay (id.). Two affected individuals, distantly related due to the founder effect of this Iceland-specific disorder, were tested to determine whether genomic cycle enrichment could be used to identify the mutation associated with the disease.

Initial Treatment of Samples and Methylation

A sample of DNA from each individual was obtained from a blood sample acquired by venipuncture. DNA from each individual (12.5 µg) was separately digested by the restriction endonuclease, PstI, at a concentration of 10 units/µg DNA, using the following mixture:

| | |
|---|---|
| PstI (100 units/μl) | 2.5 μl |
| 10x Buffer 3 | 100 μl |
| 100x BSA | 10 μl |
| dH$_2$O | up to 1000 μl |
| TOTAL: | 1000 μl |

Buffer 3: 100 mM NaCl, 50 mM Tris-HCl, 10 mM MgCl$_2$, 1 mM dithiothreitol (pH 7.9 at 25° C.).

The PstI was refreshed (2.5 μl) after 2 hours, after which the mixture was incubated at 37° C. overnight. The digested DNA was then precipitated in 100% ethanol (3 volumes) for 30 minutes at −80° C., and then centrifuged for 30 minutes at 4° C. The supernatant was removed, and the pellet was vacuum dried for 20 minutes.

The sample not to be methylated was resuspended in 67.5 μl dH$_2$O and the sample to be methylated was resuspended in 105 μl dH$_2$O. Five μl of each sample was run on an 0.8% agarose gel to confirm digestion.

The sample to be methylated was incubated with dam methylase, at a concentration of 10 units/μg DNA. For each reaction, the following mixture was used:

| | |
|---|---|
| DNA | 100 μl |
| dH$_2$O | 147.9 μl |
| 10x dam methylase buffer | 31.25 μl |
| dam methylase (8 units/μl) | 31.25 μl |
| S-adenosylmethionine (32 mM) | 1.6 μl |
| TOTAL: | 312.5 μl. |

Dam methylase buffer: 50 mM Tris-HCl (pH 7.5), 10 mM EDTA, 5 mM 2-mercaptoethanol.

The S-adenosylmethionine was refreshed (1.6 μl) after 2 hours, after which the mixture was incubated at 37° C. for an additional 2 hours. The DNA was then precipitated in 100% ethanol (3 volumes) for 30 minutes at −80° C., and then centrifuged for 30 minutes at 4° C. The supernatant was removed and the pellet was vacuum dried for 20 minutes. The sample was resuspended in 62.5 μl dH$_2$O.

The Formamide Phenol Emulsion Reassociation Technique (FPERT)

The Formamide Phenol Emulsion Reassociation Technique (FPERT) was then used (see, e.g., Casna et al. (Nucleic Acids Res. 14:7285–7303 (1986); Kohne, D. E. et al., Biochemistry 16(24):5329–41 (1977)). The unmethylated sample and the methylated sample were mixed together, giving a total volume of 125 μl of sample mixture. The sample mixture was then heat denatured at 95° C. for 10 minutes, and then re-annealed using the following FPERT reaction mixture:

Sample mixture (mixture of the unmethylated and methylated samples): 125 μl

| | |
|---|---|
| 2x FPERT mix* | 250 μl |
| Formamide | 40 μl |
| dH$_2$O | 85 μl |
| TOTAL: | 500 μl. |

*FPERT mix: for each 100 ml, 2 M Na thiocyanate (22 g), 10 mM Tris HCl (210 mg), 0.1 mM EDTA (5 mg), and formamide (8 ml).

Washed, tris-buffered phenol was added to the FPERT reaction mixture until an emulsion just formed (100–125 μl); the mixture was then agitated for 17–24 hours at room temperature. The DNA was then precipitated in 100% ethanol (3 volumes) for 30 minutes at −80° C., and then centrifuged for 30 minutes at 4° C. The supernatant was removed and the pellet was vacuum dried for 20 minutes. The resultant annealed DNA sample was resuspended in 102.5 μl dH$_2$O. The DNA yield was assessed using a cling film "spotting" approach under UV light (Molecular Cloning, A Laboratory Manual, 2nd ed. (eds. Sambrook et al.) CSHL Laboratory Press, Cold Spring Harbor, N.Y. 1989, E5–E6). To do so, 2.5 μl of annealed DNA sample was spotted with 2.5 μl of ethidium bromide (2 μg/ml) and the intensity was compared against a water control.

The FPERT reaction mixture yields an annealed DNA sample containing three possible types of DNA complexes: completely methylated homohybrids, completely unmethylated homohybrids, and "hemi-methylated" heterohybrids (which represent the annealing of single-stranded DNA from each individual). The hemi-methylated heterohybrids which are formed from the exact matching of single-stranded DNA from each sample represent the IBD fragments shared between the two individuals.

Digestion of Homohybrids

To digest (and therefore minimize the presence of) homohybrids of methylated DNA and of unmethylated DNA from the hybridized DNA sample, the hybridized DNA sample was digested with DpnI (which digests methylated, double-stranded DNA) and MboI (which digests unmethylated, double-stranded DNA). For each reaction, the following digestion mixture was used:

| | |
|---|---|
| Hybridized DNA sample (template) | 100 μl |
| DpnI (20 units/μl) | 5 μl |
| MboI (5 units/μl) | 5 μl |
| 10x Buffer 4 | 60 μl |
| 100x BSA | 6 μl |
| dH$_2$O | 424 μl |
| TOTAL: | 500 μl. |

Buffer 4: 50 mM potassium acetate, 20 mM Tris-acetate, 10 mM magnesium acetate, 1 mM dithiothreitol (pH 7.9 at 25° C.).

The digestion mixture was incubated at 37° C. for 2 hours. The DNA was then precipitated in 100% ethanol (3 volumes) for 30 minutes at −80° C., and then centrifuged for 30 minutes at 4° C. The supernatant was removed and the pellet was vacuum dried for 20 minutes. The resultant digested DNA sample was resuspended in 202.5 μl dH$_2$O. The DNA yield was assessed using a cling film "spotting" approach under UV light (Molecular Cloning, A Laboratory Manual, 2nd ed. (eds. Sambrook et al.) CSHL Laboratory Press, Cold Spring Harbor, N.Y. 1989, E5–E6). To do so, 2.5 μl of digested DNA sample was spotted with 2.5 μl of ethidium bromide (2 μg/ml) and the intensity was compared against a water control. The digested DNA sample contains heterohybrid DNA. Before removing mismatched heterohybrid DNA, the digested DNA samples were divided into four 40 μl aliquots.

Removal of Mismatched Heterohybrids

T7 endonuclease I was used to remove mismatched heterohybrids, using the following mismatch reaction mixture:

| | |
|---|---|
| T7 endonuclease I (1:100 dilution) | 1 μl |
| EndoI 10x buffer** | 29 μl |
| Template (digested DNA sample containing heterohybrid DNA) | 50 μl |

-continued

| | |
|---|---|
| dH₂O | 129 µl |
| TOTAL: | 200 µl. |

**Endol buffer: 50 mM DTT (stock, 1 M, for 3 ml, 150 µl); 100 mM MgCl₂ (stock, 1 M, for 3 ml, 300 µl); 500 nM Tris-HCl, pH 8.0 (stock, 1 M, for 3 ml, 1500 µl); 1 mg/ml BSA (stock, 10 mg/ml, for 3 ml, 300 µl).

The mismatch reaction mixture was incubated at 37° C. for 30 minutes; 50 units of exonuclease III (approximately 25 units/µg DNA) was added, and the mixture was incubated for an additional 45 minutes. The ExoIII was then inactivated at 75° C. for 15 minutes. The DNA was then precipitated in 100% ethanol (3 volumes) for 30 minutes at −80° C., and then centrifuged for 30 minutes at 4° C. The supernatant was removed and the pellet was vacuum dried for 20 minutes. The resultant perfect-match DNA sample was resuspended in 30 µl dH₂O.

To remove repetitive sequences with PstI overhangs from the perfect-match DNA sample, the perfect-match DNA samples (containing perfect-match DNA heterohybrids) were incubated with COT-1 (GIBCO) at 95° C. for 10 minutes and then allowed to cool to room temperature for 1 hour.

Amplification of Sequences

To amplify the perfect-match heterohybrids with PstI overhangs, adaptors were ligated to each end of the perfect-match DNA heterohybrids (long adaptor oligo, AGCTA-CATGGTAGATCGAATTCTCACTGCA (SEQ ID NO:1); short adaptor oligo, GTGAGAATTCGATCTACCATGTAGCT-phosphorylated (SEQ ID NO:2). The PstI adaptor solution (1 µM) was generated by heating the adaptor oligonucleotides to 95° C. for 5 minutes, and then allowing the oligonucleotides to re-anneal by slowly dropping the temperature to 50° C. The ligation reaction mixture included the following:

| | |
|---|---|
| Perfect-match DNA heterohybrids | 5 µl |
| 10x ligation buffer | 1 µl |
| DNA ligase (400 U/µl) | 0.1–0. µl |
| Adaptor oligonucleotide (1 µM) | 1 µl |
| dH₂O | 2.5–2.9 µl (10 µl) |
| TOTAL: | 10 µl. |

The ligation reaction mixture was incubated at room temperature for 3 hours, along with the following controls: dH₂O plus adaptor, PstI-digested DNA plus adaptor, PstI-digested DNA minus adaptor. The resultant perfect-match DNA heterohybrid ligations were column-cleaned using the QIAquick PCR Purification kit (Qiagen). The flow-through was collected in 50 µl.

Long-range PCR

Long-range PCR was performed to enhance the perfect-match DNA heterohybrid ligations. Long-range PCR is described in detail in U.S. patent application Ser. No. 09/391,244, the entire teachings of which are incorporated herein by reference. The long-range PCR reaction mixture was as follows:

| | |
|---|---|
| Perfect-match DNA heterohybrid ligations | 6 µl |
| 3.3x Buffer | 9.0 µl (final - 1x) |
| MgOAc | 1.2 µl (final - 1 mM) |
| dNTP (2 mM) | 3 µl (final - 200 µM) |
| GCE primer (µM)*** | 3 µl (final - 0.5 µM) |

-continued

| | |
|---|---|
| rTth pol mix | 0.6 µl (final - 0.6 U) |
| dH₂O | 7.2 µl. |
| TOTAL: | 30 µl |

***GCE primer: AGCTACATGGTAGATCGAATTCTCACTGCAG (SEQ ID NO:3).

The 24 µl mixture was added to the 6 µl of DNA fragments (template) and immediately placed in the thermocycler of rTth pol exonuclease activity. The following cycle was used (PE9600 GeneAmp): 1 cycle at 94° C. for 30 seconds; 35 cycles at 90° C. for 10 seconds, 60° C. for 10 seconds, and 65° C. for 10 minutes.

Between 5–10 µl of the resultant PCR products was run on 0.8% agarose gel. The DNA was isolated from the gel using the Prep-a-Gene" kit (Biorad), in order to select different sizes of PCR products of the perfect-match DNA heterohybrid ligations for BAC probing.

BAC Probing To perform BAC probing, the PCR products containing the perfect-match DNA heterohybrid ligations were first labeled by mixing approximately 10–20 µl of PCR products with 12–22 µl dH₂O heating to 95° C. for 5 minutes, cooling on ice, and then incubating for 1–4 hours at 37° C. with the following: α32P dCTP (10 mCi/ml) (7 µl); 5×oligolabeling mix (10 µl), and Klenow fragment (1 µl) (Amersham Pharmacia Biotech).

The labeled PCR products were added to prehybridized (Rapidhyb for 2 hours at 65° C.) BAC membranes, and hybridized for 16 hours at 65° C. The BAC membranes included a 400-random membrane, and a reference membrane that was generated using RFLP-PCR products known to include the mutation associated with the disease. The membranes were then washed twice for 30 minutes with 2×SSC+0.1% SDS at 65° C. If the radioactivity was high (?4,000–5,000 cpm), the membranes were washed with 0.1×SSC+0.1% SDS until the radioactivity level had dropped under 4,000 cpm. The membranes were then rinsed 5 times in 6×SSC for 20 seconds at room temperature to remove the remaining SDS. The membranes were dried for 10 minutes on Whatman paper, and placed between cling-film layers (Pelicola). They were then placed in a cassette with MS X-ray film (Kodak) and exposed at −70° C. for the appropriate time (approximately 2 to 48 hours, depending on the signal), and then developed. The results indicated that the mutation was identified in the PCR products, thereby indicating that the mutation can be identified by the genomic cycle enrichment methods described herein.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of identifying perfectly-matched heterohybrid DNA fragments which comprise DNA that is identical by descent for two individuals, comprising:
   a) obtaining a sample of genomic DNA from each of two individuals, thereby providing a first sample of genomic DNA and a second sample of genomic DNA;
   b) contacting the first and the second sample of genomic DNA with restriction endonuclease, thereby forming a first and a second preliminary digest DNA sample, respectively;
   c) methylating a first preliminary digest DNA sample, thereby forming a methylated preliminary digest DNA sample;
   d) mixing the methylated preliminary digest DNA sample and the second preliminary digest DNA sample, thereby forming a DNA sample mixture;
   e) incubating the DNA sample mixture under conditions which allow denaturation of the DNA samples, thereby forming a denatured DNA sample mixture;
   f) incubating the denatured DNA sample mixture under conditions which allow re-annealing of the DNA samples, thereby forming an annealed DNA sample mixture comprising homohybrid DNA fragments and heterohybrid DNA fragments;
   g) contacting the annealed DNA sample mixture with restriction endonuclease to digest homohybrid DNA fragment, thereby forming a homohybrid-digested, annealed DNA sample mixture; and
   h) contacting the homohybrid-digested, annealed DNA sample mixture with endonuclease to cleave both strands of a mismatch-containing heterohybrid DNA fragments, wherein the endonuclease is a methylation-independent endonuclease that recognize all eight possible mismatches, the endonuclease comprising T7 endonuclease I or T4 endonuclease VII, thereby forming a mismatch-digested DNA sample mixture comprising perfectly-matched heterohybrid DNA fragments, without performing a benzoylated, naphthylated DEAE cellulose step, wherein the perfectly-matched heterohybrid DNA fragments comprise DNA fragments that are identical by descent for the two individuals.

2. The method of claim 1, wherein the restriction endonuclease of step (b) is PstI.

3. The method of claim 1, wherein conditions which allow denaturation of the DNA samples in step (e) comprise heating the DNA sample mixture to approximately 85–99° C.

4. The method of claim 1, wherein the conditions which allow re-annealing of the DNA samples of step (f) comprise incubating the denatured DNA sample mixture in the presence of a phenol based emulsion.

5. The method of claim 1, wherein the restriction endonucleases which digest homohybrid DNA fracts of step (g) comprise DpnI and MboI.

6. The method of claim 1, wherein the methylation-independent endonuclease that recognizes all eight possible mismatches of step (h) comprises T7 endonuclease I.

7. The method of claim 6, further comprising incubating the mismatch-digested DNA sample mixture comprising perfectly-matched heterohybrid DNA fragments of step (h)

with an exonuclease that digests DNA fragments with non-specific 5' overhangs.

8. The method of claim 7, wherein the exonuclease is Exonuclease III.

9. The method of claim 8, further comprising incubating the mismatch-digested DNA sample mixture comprising perfectly-matched heterohybrid DNA fragments of step (h) with a sample of repetitive DNA under conditions which allow small fragments that are rich in repetitive sequences to hybridize with the repetitive DNA.

10. The method of claim 9, wherein the sample of repetitive DNA comprises COT-1 DNA.

11. The method of claim 10, further comprising ligating nucleic acid adaptors to the perfectly-matched heterohybrid DNA fragments.

12. The method of claim 11, further comprising performing long-range polymerase chain reaction to amplify perfectly-matched heterohybrid DNA fragments ligated to the nucleic acid adaptors.

13. The method of claim 1, further comprising repeating steps (b) through (h) utilizing perfectly-matched heterohybrid DNA fragments as a first sample of genomic DNA, and a sample of genomic DNA from a third individual as a second sample of genomic DNA.

14. A method of identifying perfectly-matched heterohybrid DNA fragments which comprise DNA that is identical by descent for two individuals, comprising:
   a) obtaining a sample of genomic DNA from each of two individuals, thereby providing a first sample of genomic DNA and a second sample of genomic DNA;
   b) contacting the first and the second sample of genomic DNA with restriction endonuclease PstI, thereby forming a first and a second preliminary digest DNA sample;
   c) methylating a first preliminary digest DNA sample, thereby forming a methylated preliminary digest DNA sample;
   d) mixing the methylated preliminary digest DNA sample and the second preliminary digest DNA sample, thereby forming a DNA sample mixture;
   e) incubating the DNA sample mixture under conditions which allow denaturation of the DNA samples, thereby forming a denatured DNA sample mixture;
   f) incubating the denatured DNA sample mixture under conditions which allow re-annealing of the DNA samples, the conditions comprising incubating in the presence of a phenol based emulsion, thereby forming an annealed DNA sample mixture comprising homohybrid DNA fragments and heterohybrid DNA fragments;
   g) contacting the annealed DNA sample mixture with restriction endonucleases DpnI and MboI, thereby forming a homohybrid-digested, annealed DNA sample mixture; and
   h) contacting the homohybrid-digested, annealed DNA sample mixture with T7 endonuclease I, thereby forming a mismatch-digested DNA sample mixture comprising perfectly-matched heterohybrid DNA fragments,
wherein the perfectly-matched heterohybrid DNA fragments comprise DNA fragments that are identical by descent for the two individuals.

15. The method of claim 14, further comprising incubating the mismatch-digested DNA sample mixture comprising perfectly-matched heterohybrid DNA fragments of step (h) with Exonuclease III.

16. The method of claim 15, further comprising incubating the mismatch-digested DNA sample mixture comprising perfectly-matched heterohybrid DNA fragments of step (h) with a sample of repetitive DNA under conditions which allow small fragments that are rich in repetitive sequences to hybridize with the repetitive DNA.

17. The method of claim 16, wherein the sample of repetitive DNA comprises COT-1 DNA.

18. The method of claim 17, further comprising ligating nucleic acid adaptors to the perfectly-matched heterohybrid DNA fragments.

19. The method of claim 18, further comprising performing long-range polymerase chain reaction to amplify perfectly-matched heterohybrid DNA fragments ligated to the nucleic acid adaptors.

20. The method of claim 14, further comprising repeating steps (b) through (h) utilizing perfectly-matched heterohybrid DNA fragments as a first sample of genomic DNA, and a sample of genomic DNA from a third individual as a second sample of genomic DNA.

21. A method of identifying perfectly-matched heterohybrid DNA fragments which comprise DNA that is identical by descent for two individuals, comprising:
   a) obtaining a sample of genomic DNA from each of two individuals, thereby providing a first sample of genomic DNA and a second sample of genomic DNA;
   b) contacting the first and the second sample of genomic DNA with restriction endonuclease PstI, thereby forming a first and a second preliminary digest DNA sample;
   c) methylating a first preliminary digest DNA sample, thereby forming a methylated preliminary digest DNA sample;
   d) mixing the methylated preliminary digest DNA sample and the second preliminary digest DNA sample, thereby forming a DNA sample mixture;
   e) incubating the DNA sample mixture under conditions which allow denaturation of the DNA samples, thereby forming a denatured DNA sample mixture;
   f) incubating the denatured DNA sample mixture under conditions which allow re-annealing of the DNA samples, the conditions comprising incubating in the presence of a phenol based emulsion, thereby forming an annealed DNA sample mixture comprising homohybrid DNA fragments and heterohybrid DNA fragments;
   g) contacting the annealed DNA sample mixture with restriction endonucleases DpnI and MboI, thereby forming a homohybrid-digested, annealed DNA sample mixture;
   h) contacting the homohybrid-digested, annealed DNA sample mixture with T7 endonuclease I, thereby forming a mismatch-digested DNA sample mixture comprising perfectly-matched heterohybrid DNA fragments,;
   i) incubating the mismatch-digested DNA sample mixture comprising perfectly-matched heterohybrid DNA fragments of step (h) with an Exonuclease III;
   j) incubating the mismatch-digested DNA sample mixture comprising perfectly-matched heterohybrid DNA fragments of step (h) with a sample of COT-1 DNA under conditions which allow small fragments that are rich in repetitive sequences to hybridize with the COT-1 DNA;
   k) ligating nucleic acid adaptors to the perfectly-matched heterohybrid DNA fragments; and l) performing long-range polymerase chain reaction to amplify perfectly-matched heterohybrid DNA fragments ligated to the nucleic acid adaptors, wherein the perfectly-matched heterohybrid DNA fragments comprise DNA fragments that are identical by descent for the two individuals.

22. The method of claim 1, wherein the methylation-independent endonuclease that recognizes all eight possible mismatches of step (h) comprises T4 endonuclease VII.

23. The method of claim 22, further comprising incubating the mismatch-digested DNA sample mixture comprising perfectly-matched heterohybrid DNA fragment of step (h) with an exonuclease that digests DNA fragment with non-specific 5' overhangs.

24. The method of claim 23, wherein the exonuclease is Exonuclease III.

25. The method of claim 24, further comprising incubating the mismatch-digested DNA sample mixture comprising perfectly-matched heterohybrid DNA fragments of step (h) with a sample of repetitive DNA under conditions which allow small fragments that are rich in repetitive sequence to hybridize with the repetitive DNA.

26. The method of claim 25, wherein the sample of repetitive DNA comprises COT-1 DNA.

27. The method of claim 26, further comprising ligating nucleic acid adaptor to the perfectly-method heterohybrid DNA fragment.

28. The method of claim 27, further comprising performing long-range polymerase chain reaction to amplify perfectly-matched heterohybrid DNA fragments ligated to the nucleic acid adaptors.

* * * * *

UNITED STATES PATENT AND TRADEMARK OFFICE
CERTIFICATE OF CORRECTION

PATENT NO.    : 6,524,794 B1
DATED         : February 25, 2003
INVENTOR(S)   : Struan Grant and Thorarinn Blöndal It is certified that error appears in the above-identified patent and that said Letters Patent is hereby corrected as shown below:

Column 12,
Line 60, delete "fracts" and insert -- fragments --.

Column 15,
Lines 12 and 13, delete "fragment" and insert -- fragments --.

Column 16,
Line 10, delete "method" and insert -- matched --.
Line 10, delete "adaptor" and insert -- adaptors --.
Line 11, delete "fragment" and insert -- fragments --.

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,524,794 B1
DATED        : February 25, 2003
INVENTOR(S)  : Struan Grant and Thorarian Blöndal It is certified that error appears in the above-identified patent and that said Letters Patent is hereby corrected as shown below:

Drawings,
Figure, delete "genomic cycle enrichment (GCE)" and insert
-- Identical-By-Descent Fragment Enrichment (IBDFE) --.

Column 1,
Line 11, delete "indentif" and insert -- identify --.

Column 2,
Lines 20-21, delete "genomic cycle enrichment (GCE)" and insert
-- Identical-By-Descent Fragment Enrichment (IBDFE) --.

Signed and Sealed this

First Day of July, 2003

JAMES E. ROGAN
*Director of the United States Patent and Trademark Office*

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Man-made oligonucleotide

<400> SEQUENCE: 1
agctacatgg tagatcgaat tctcactgca                                   30

<210> SEQ ID NO 2
<211> LENGTH: 26
<212> TYPE: DNA
<213> ORGANISM: Artificial Sequence
<220> FEATURE:
<223> OTHER INFORMATION: Man-made oligonucleotide

<400> SEQUENCE: 2
gtgagaattc gatctaccat gtagct                                       26

<210> SEQ ID NO 3
<211> LENGTH: 31
<212> TYPE: DNA
<213> ORGANISM: Artificial Sequence
<220> FEATURE:
<223> OTHER INFORMATION: Man-made oligonucleotide

<400> SEQUENCE: 3
agctacatgg tagatcgaat tctcactgca g                                 31